United States Patent [19]

Dahmen et al.

[11] Patent Number: 5,990,048
[45] Date of Patent: Nov. 23, 1999

[54] SELECTIVE HERBICIDES BASED ON METRIBUZIN AND SUBSTITUTED IMIDAZO [1,2-A]PYRIDIN-3-YL-SULFONYL COMPOUNDS

[75] Inventors: Peter Dahmen, Neuss; Markus Dollinger; Hans-Joachim Santel, both of Leverkusen; Hans-Jochem Riebel, Wuppertal, all of Germany

[73] Assignee: Bayer Aktiengesellschaft, Leverkusen, Germany

[21] Appl. No.: 08/931,326

[22] Filed: Sep. 16, 1997

[30] Foreign Application Priority Data

Sep. 23, 1996 [DE] Germany .............. 196 38 886

[51] Int. Cl.⁶ .............. A01N 43/707; A01N 43/54; A01N 43/64
[52] U.S. Cl. .............. 504/134; 504/133; 504/135; 504/136
[58] Field of Search .............. 504/133, 134, 504/135, 136

[56] References Cited

U.S. PATENT DOCUMENTS

| | | | |
|---|---|---|---|
| 3,671,523 | 6/1972 | Westphal et al. | 544/182 |
| 3,905,801 | 9/1975 | Fawzi | 504/229 |
| 5,173,104 | 12/1992 | Feucht | 504/133 |
| 5,223,016 | 6/1993 | Takematsu et al. | 504/130 |
| 5,420,098 | 5/1995 | Ansai et al. | 504/133 |

FOREIGN PATENT DOCUMENTS

| | | |
|---|---|---|
| 0 305 939 | 3/1989 | European Pat. Off. . |
| 0 477 808 | 4/1992 | European Pat. Off. . |
| 17 95 784 | 6/1975 | Germany . |

Primary Examiner—John Pak
Attorney, Agent, or Firm—Sprung Kramer Schaefer & Briscoe

[57] ABSTRACT

The novel herbicidally active compound combinations comprising (a) metribuzin of the formula (I) and (b) an active compound from the group of the substituted imidazo[1,2-a] pyridin-3-yl-sulfonyl compounds of the formula (II)

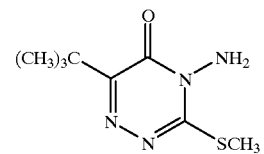

(I)

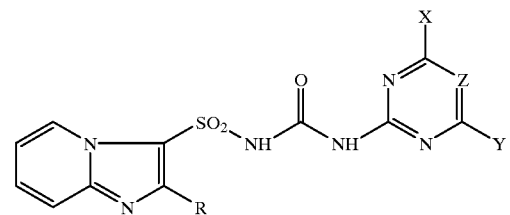

(II)

where

Z represents N or CH and

R, X and Y are each as defined in the description, exhibit synergistic activities at certain weight ratios and can be used as selective herbicides in a variety of crop plants (for example maize, wheat and barley).

5 Claims, No Drawings

SELECTIVE HERBICIDES BASED ON METRIBUZIN AND SUBSTITUTED IMIDAZO [1,2-A]PYRIDIN-3-YL-SULFONYL COMPOUNDS

The invention relates to novel herbicidal synergistic active compound combinations comprising metribuzin (4-amino-6-t-butyl-3-methylthio-1,2,4-triazin-5(4H)-one) and certain substituted imidazo[1,2-a]pyridin-3-yl-sulfonyl compounds, which can be used particularly advantageously for selective weed control in a variety of crop plants.

The active compound metribuzin has been known for a long time (cf. DE-1-795 784, U.S. Pat. No. 3,905,801) and has proved useful for the selective control of weeds, in particular in soybean and potato. However, the activity profile and the lack of compatibility make use difficult in other crops, such as in maize, wheat and barley. Additionally, it would be desirable to lower the application rates in weed control.

Certain substituted imidazo[1,2-a]pyridin-3-yl-sulfonyl compounds have been disclosed as herbicides for the selective control of weeds in rice and wheat (cf. EP-305 939, EP-477 808). However, these compounds have a number of gaps in their activity spectrum.

Surprisingly, it has now been found that the active compound metribuzin when applied together with known substituted imidazo[1,2-a]pyridin-3-yl-sulfonyl compounds exhibits pronounced synergistic effects in respect of the activity against weeds and can be used particularly advantageously in broad spectrum combination products for the selective control of weeds in crops, for example maize, wheat and barley.

The present invention accordingly provides synergistic selective herbicidal compositions characterized by a content of an active compound combination comprising (a) metribuzin of the formula (I)

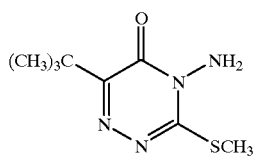

(I)

and (b) an active compound from the group of the substituted imidazo[1,2-a]pyridin-3-yl-sulfonyl compounds of the general formula (II)

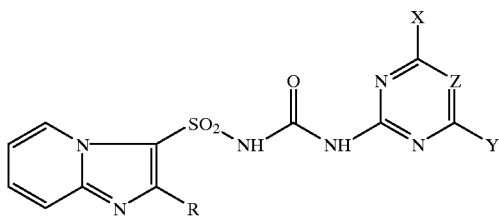

(II)

in which
R represents halogen or represents optionally substituted alkyl alkoxy, alkoxycarbonyl, alkylthio, alkylsulfinyl, alkylsulfonyl, alkylamino or dialkylamino,
X represents hydrogen, halogen or represents respectively optionally substituted alkyl, alkoxy, alkylthio, alkylsulfinyl, alkylsulfonyl, alkylamino, dialkylamino or cycloalkyl,
Y represents hydrogen, halogen or represents respectively optionally substituted alkyl, alkoxy, alkylthio, alkylsulfinyl, alkylsulfonyl, alkylamino, dialkylamino or cycloalkyl, and
Z represents nitrogen or a CH grouping, 0.001 to 100 parts by weight of an active compound of the formula (II) being employed per part by weight of active compound of the formula (I).

Of particular interest are herbicidal compositions according to the invention which are characterized by a content of an active compound combination comprising (a) metribuzin of the formula (I)—above—and (b) an active compound from the group of the substituted imdazo[1,2-a]pyridin-3-yl-sulfonyl compounds of the general formula (II)—above—in which
R represents halogen or represents respectively optionally cyano-, halogen- or $C_1$–$C_4$-alkoxy-substituted alkyl, alkoxy, alkoxy-carbonyl, alkylthio, alkylsulfinyl, alkylsulfonyl, alkylamino or dialkylamino having in each case 1 to 6 carbon atoms in the alkyl groups,
X represents hydrogen, halogen, or represents respectively optionally halogen- or $C_1$–$C_4$-alkoxy-substituted alkyl, alkoxy, alkylthio, alkylsulfinyl, alkylsulfonyl, alkylamino or dialkylamino having in each case 1 to 6 carbon atoms in the alkyl groups or represents cycloalkyl having 3 to 6 carbon atoms,
Y represents hydrogen, halogen, or represents respectively optionally halogen- or $C_1$–$C_4$-alkoxy-substituted alkyl, alkoxy, alkylthio, alkylsulfinyl, alkylsulfonyl, alkylamino or dialkylamino having in each case 1 to 6 carbon atoms in the alkyl groups or represents cycloalkyl having 3 to 6 carbon atoms, and
Z represents nitrogen or a CH grouping.

Of very particular interest are herbicidal compositions according to the invention which are characterized by a content of an active compound combination comprising (a) metribuzin of the formula (I)—above—and (b) an active compound from the group of the substituted imdazo[1,2-a] pyridin-3-yl-sulfonyl compounds of the general formula (II)—above—in which
R represents fluorine chlorine, bromine or represents respectively optionally fluorine-, chlorine-, methoxy- or ethoxy-substituted methyl, ethyl, methoxy, ethoxy, n- or i-propoxy, methoxycarbonyl, ethoxycarbonyl, n- or i-propoxycarbonyl, methylthio, ethylthio, n- or i-propylthio, methylsulfinyl, ethylsulfinyl, n- or i-propylsulfinyl, methylsulfonyl, ethylsulfonyl, n- or i-propylsulfonyl, methylamino, ethylamino, n- or i-propylamino, dimethylamino or diethylamino,
X represents hydrogen, fluorine, chlorine, bromine, or represents respectively optionally fluorine-, chlorine-, methoxy- or ethoxy-substituted methyl, ethyl, methoxy, ethoxy, n- or i-propoxy, methylthio, ethylthio, n- or i-propylthio, methylsulfinyl, ethylsulfinyl, n- or i-propylsulfinyl, methylsulfonyl, ethylsulfonyl, n- or i-propylsulfonyl, methylamino, ethylamino, n- or i-propylamino, dimethylamino or diethylamino, or represents cyclopropyl,
Y represents hydrogen, fluorine, chlorine, bromine, or represents respectively optionally fluorine-, chlorine-, methoxy- or ethoxy-substituted methyl, ethyl, methoxy, ethoxy, n- or i-propoxy, methylthio, ethylthio, n- or i-propylthio, methylsulfinyl, ethylsulfinyl, n- or i-propylsulfinyl, methylsulfonyl, ethylsulfonyl, n- or i-propylsulfonyl, methylamino, ethylamino, n- or i-propylamino, dimethylamino or diethylamino, or represents cyclopropyl, and Z represents nitrogen or a CH grouping.

Specific examples of the compounds of the formula (II) to be used as mixing partners according to the invention are: 2-fluoro-N-[[(4,6-dimethoxy-pyrimidin-2-yl)amino]carbonyl]-imidazo[1,2-a]pyridine-3-sulfonamide, 2-chloro-N-[[(4,6-dimethoxy-pyrimidin-2-yl)amino]carbonyl]-imidazo[1,2-a]pyridine-3-sulfonamide, 2-bromo-N-[[(4,6-dimethoxy-pyrimidin-2-yl)amino]carbonyl]-imidazo[1,2-a]pyridine-3-sulfonamide, 2-methoxy-N-[[(4,6-dimethoxy-pyrimidin-2-yl)amino]carbonyl]-imidazo[1,2-a]pyridine-3-sulfonamide, 2-ethoxy-N-[[(4,6-dimethoxy-pyrimidin-2-yl)amino]carbonyl]-imdazo[1,2-a]pyridine-3-sulfonamide, 2-methylthio-N-[[(4,6-dimethoxy-pyrimidin-2-yl)amino]carbonyl]-imidazo [1,2-a]pyridine-3-sulfonamide, 2-ethylthio-N-[[(4,6-dimethoxy-pyrimidin-2-yl)amino]carbonyl]-imidazo[1,2-a]pyridine-3-sulfonamide, 2-methylsulfinyl-N-[[(4,6-dimethoxy-pyrimidin-2-yl)amino]carbonyl]-imidazo[1,2-a]pyridine-3-sulfonamide, 2-ethylsulfinyl-N-[[(4,6-dimethoxy-pyrimidin-2-yl)amino]carbonyl]-imidazo[1,2-a]pyridine-3-sulfonamide, 2-methylsulfonyl-N-[[(4,6-dimethoxy-pyrimidin-2-yl)amino]carbonyl]-imidazo[1,2-a]pyridine-3-sulfonamide,2-ethylsulfonyl-N-[[(4,6-dimethoxy-pyrimidin-2-yl)amino]carbonyl]-imidazo[1,2-a]pyridine-3-sulfonamide.

Especially preferred as components of mixtures of compounds of the formulae (I) and (II) are the active compounds metribuzin (4-amino-6-t-butyl-3-methylthio-1,2,4-triazin-5 (4H)-one) and sulfosulfurone (2-ethylsulfonyl-N-[[(4,6-dimethoxy-pyrimidin-2-yl)amino]carbonyl]-imidazo[1,2-a]pyridine-3-sulfonamide.

Surprisingly, it has now been found that the active compound combinations of metribuzin of the formula (I) and substituted imidazo[1,2-a]pyridin-3-yl-sulfonyl compounds of the general formula (II) defined above combine very good tolerability by crops with particularly high herbicidal activity and can be used for the selective control of weeds in a variety of crops, such as, for example, maize, wheat and barley.

Surprisingly, the herbicidal activity of the active compound combinations according to the invention comprising the active compound metribuzin of the formula (I) and compounds of the general formula (II) is considerably higher than the sum total of the activities of the individual active compounds.

This means that an unforeseeable synergistic effect is present and not just complementation. The novel active compound combinations are well tolerated by many crop plants, and even weeds which are otherwise difficult to control are efficiently controlled by the novel active compound combinations. The novel active compound combinations are therefore a useful addition to the range of the selective herbicides. The active compound combinations according to the invention can be used for example in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.

Dicotyledonous crop plants of the genera: Gossypium, Glycine, Beta, Daucus, Phaseolus, Pisum, Solanum, Linum, lpomoea, Vicia, Nicotiana, Lycopersicon, Arachis, Brassica, Lactuca, Cucumis, Cuburbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera, Phalaris.

Monocotyledonous crop Dlants of the genera: Oryza, Zea, Triticum, Hordeum, Avena, Secale, Sorghum, Panicum, Saccharum, Ananas, Asparagus, Allium.

However, the use of the active compound combinations according to the invention is in no way restricted to these genera, but also extends in the same manner to other plants.

The synergistic effect of the active compound combinations according to the invention is especially pronounced at specific concentration ratios. However, the weight ratios of the active compounds in the active compound combinations can be varied within relatively wide ranges. In general, 0.001 to 100 parts by weight, preferably 0.005 to 50 parts by weight, especially preferably 0.02 to 20 parts by weight, of active compound of the general formula (II) are used per part by weight of active compound metribuzin of the formula (I).

The active compound combinations can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, i.e. emulsifiers and/or dispersants and/or foam-formers.

If water is used as an extender, organic solvents can, for example, also be used as auxiliary solvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulfoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and protein hydrolyzates; suitable dispersants are: for example lignin-sulfite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

In general, the active compound combinations according to the invention are applied in the form of ready mixes. However, the active compounds in the active compound combinations can also be formulated individually and mixed upon application, that is to say applied in the form of tank mixes.

The new active compound combinations as such or in the form of their formulations can also be used as mixtures with further known herbicides, finished formulations or tank mixes again being possible. Mixtures with other known active compounds such as fungicides, insecticides, acaricides, nemtaticides, bird repellants, growth promoters, plant nutrients and soil conditioners, are also possible. Furthermore, it may be advantageous for specific purposes, in particular when using the post-emergence method, to incorporate mineral or vegetable oils tolerated by plants (for example "Oleo Dupont 11E", which is commercially available) or ammonium salts such as, for example, ammonium sulfate or ammonium thiocyanate, as further additives in the formulations.

The novel active compound combinations according to the invention can be used as such, in the form of their formulations or in the use forms prepared therefrom by further dilution, such as ready-to-use solutions, suspensions emulsions. powders, pastes and granules. They are used in the customary manner, for example by watering, spraying, atomizing, dusting or spreading.

The active compound combinations according to the invention can be applied before or after the emergence of the plants, ie. by the pre-emergence and by the post-emergence method. They can also be incorporated into the soil prior to sowing.

The rates of application of the active compound combinations according to the invention can be varied within a certain range; they depend, inter alia, on the weather and on the condition of the soil. In general, the rates of application are between 10 g and 10 kg per ha, preferably between 50 g and 5 kg per ha, in particular between 100 g and 2 kg per ha.

The good herbicidal activity of the novel active compound combinations is evident from the examples below. While the individual active compounds show weaknesses in their herbicidal activity, the combinations all exhibit very efficient control of weeds, and this control exceeds a simple sum of the activities.

In herbicides, a synergistic effect is always present when the herbicidal activity of the active compound combination exceeds that of the active compounds applied individually.

The expected activity for a given combination of two herbicides can be calculated as follows (cf. Colby, S. R.: "Calculating synergistic and antagonistic responses of herbicide combinations", Weeds 15, pages 20–22, 1967):

If X=% damage by herbicide A (active compound of formula 1) at the rate of application of p kg/ha and Y=% damage by herbicide B (active compound of formula 11) at the rate of application of q kg/ha and F=the expected damage caused by herbicides A and B at a rate of application of p and q kg/ha, then E=X+Y−(X * Y/100).

If the actual damage exceeds the calculated value, the combination is superadditive with regard to its activity, i.e. it shows a synergistic effect.

The examples below reveal that the herbicidal activity of the active compound combinations according to the invention found exceeds the calculated value, i.e. that the novel active compound combinations have a synergistic action.

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the active compound preparation in such a way as to apply the particular amounts of active compound desired per unit area. The concentration of the spray liquor is chosen such that the particular amounts of active compound desired are applied in 1000 l of water/ha. After three weeks, the degree of damage to the plants is rated in % damage in comparison to the development of the untreated control.

The figures denote:

0%=no action (like untreated control)

100% total destruction

Active compounds, application rates, test plants and results are listed in Table A below, the abbreviations used in Table A having the following meanings:

(I)=Metribuzin (4-amino-6-t-butyl-3-methylthio-1,2,4-triazin-5(4H)-one; alternative name: 4-amino-6-t-butyl-4,5-dihydro-3-methylthio-1,2,4-triazin-5-one);

(II-1)=Sulfosulfurone (2-ethylsulfonyl-N-[[(4,6-dimethoxy-pyrimidin-2-yl)amino]carbonyl]imidazo[1,2-a]pyridine-3-sulfonamide);

found=observed damge or activity (in %)

calc.=damage or activity (in %) calculated using the Colby formula

TABLE A

| Active compound or active compound combination | Post-emergence test/greenhouse | | | | |
|---|---|---|---|---|---|
| | Application rate in g/ha (of active compound) | Test plants Damage or activity in % | | | |
| | | *Apera spica-venti* | | *Setaria viridis* | |
| | | found | calc. | found | calc. |
| (I) - known - | 60 | 20 | | 50 | |
| (II-1) - known - | 15 | 80 | | 80 | |
| (I) + (II-1) - according to the invention - | 60 + 15 | 98 | 84 | 100 | 90 |

We claim:

1. An herbicidal composition comprising an active compound combination containing (a) metribuzin of the formula (I)

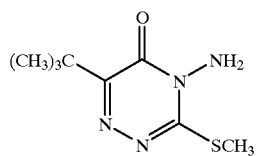

and (b) sulfosulfuron (2-ethyl-sulfonyl-N-[[(4,6-dimethoxy-pyrimidin-2-yl)amino]carbonyl]imidazo[1,2-a]pyridine-3-sulfonamide)

wherein 0.001 to 100 parts by weight of sulfosulfuron (2-ethyl-sulfonyl-N-[[(4,6-dimethoxy-pyrimidin-2-yl)amino]carbonyl]imidazo[1,2-a]pyridine-3-sulfonamide) is employed per part by weight of active compound metribuzin of the formula (I).

2. The herbicidal composition according to claim 1, wherein 0.005 to 50 parts by weight of the sulfosulfuron (2-ethyl-sulfonyl-N-[[(4,6-dimethoxy-pyrimidin-2-yl)amino]carbonyl]imidazo[1,2-a]pyridine-3-sulfonamide) is employed per part by weight of active compound metribuzin of the formula (I).

3. The herbicidal composition according to claim 2, wherein 0.02 to 20 parts by weight of sulfosulfuron (2-ethyl-sulfonyl-N-[[(4,6-dimethoxy-pyrimidin-2-yl)amino]carbonyl]imidazo[1,2-a]pyridine-3-sulfonamide) is employed per part by weight of active compound metribuzin of the formula (I).

4. A method for controlling undesired vegetation, comprising administering an herbicidally effective amount of an active compound combination according to claim 1 to said vegetation or to a locus from which it is desired to exclude said vegetation.

5. A process for preparing the herbicidal composition according to claim 1 comprising mixing the active compound combination with an extender or a surfactant.

* * * * *